(12) United States Patent
Cree et al.

(10) Patent No.: US 6,291,050 B1
(45) Date of Patent: Sep. 18, 2001

(54) TOPSHEET SYSTEMS FOR ABSORBENT ARTICLES EXHIBITING IMPROVED HYDROPHILICITY GRADIENTS

(75) Inventors: James William Cree, Mundelein, IL (US); Gregory Wade Taylor, Forest Park, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/183,768

(22) Filed: Oct. 30, 1998

(51) Int. Cl.[7] .................................................... A61F 13/15
(52) U.S. Cl. ..................... 428/131; 428/137; 428/138; 428/409; 604/370; 604/378; 604/381; 604/383
(58) Field of Search ................................ 604/370, 372, 604/378, 383, 381, 382; 428/131, 132, 137, 138, 409, 413

(56) References Cited

U.S. PATENT DOCUMENTS

| | | | |
|---|---|---|---|
| 3,911,173 | 10/1975 | Sprague, Jr. | 427/207 |
| 3,929,135 | 12/1975 | Thompson | 128/287 |
| 3,934,588 | 1/1976 | Mesek et al. | 128/290 |
| 3,955,577 | 5/1976 | Gellert et al. | 128/290 |
| 3,967,623 | 7/1976 | Butterworth et al. | 128/287 |
| 4,342,314 | 8/1982 | Radel et al. | 128/287 |
| 4,364,985 | 12/1982 | Tokuyama et al. | 428/149 |
| 4,456,570 | 6/1984 | Thomas et al. | 264/22 |
| 4,463,045 | 7/1984 | Ahr et al. | 428/131 |
| 4,535,020 | 8/1985 | Thomas et al. | 428/131 |
| 4,585,449 | 4/1986 | Karami | 604/378 |
| 4,629,457 | 12/1986 | Ness | 604/382 |
| 4,629,643 | 12/1986 | Curro et al. | 428/131 |
| 4,637,819 | 1/1987 | Ouellette et al. | 604/369 |
| 4,695,422 | 9/1987 | Curro et al. | 264/504 |
| 4,705,813 | 11/1987 | Ito et al. | 521/92 |
| 4,755,413 | 7/1988 | Morris | 428/138 |
| 4,785,996 | 11/1988 | Ziecker et al. | 239/298 |

(List continued on next page.)

FOREIGN PATENT DOCUMENTS

| | | |
|---|---|---|
| 4321155 | 1/1995 | (DE) . |
| 0198683 | 10/1986 | (EP) . |
| 0 592 884A1 | 4/1994 | (EP) . |
| 1435497 | 5/1976 | (GB) . |
| 02-168950 | 6/1990 | (JP) . |
| 07 328532A | 12/1995 | (JP) . |
| 08 131940A | 5/1996 | (JP) . |
| 09 132722A | 5/1997 | (JP) . |
| WO 87/05206 | 9/1987 | (WO) . |
| WO 93/19709 | 10/1993 | (WO) . |
| WO 94/28846 | 12/1994 | (WO) . |
| WO 95/17545 | 6/1995 | (WO) . |
| WO 98/10724 | 3/1998 | (WO) . |

*Primary Examiner*—Blaine Copenheaver
*Assistant Examiner*—Alicia Chevalier
(74) *Attorney, Agent, or Firm*—Eileen L. Hughett; Caroline Wei-Berk; Roddy M. Bullock

(57) ABSTRACT

An apertured polymeric film web having a first surface, a second surface generally parallel to and spaced apart from said first surface, and a plurality of fluid passageways extending between the first surface and the second surface to place the first surface and the second surface in fluid communication with one another. The web is formed of a polymeric film comprising at least one bulk modified layer, the bulk modified layer comprising a substantially homogeneous, stabilized dispersion comprising a comparatively low surface energy material in a polymeric material. The comparatively low surface energy material, referred to herein as a hydrophobic additive, imparts hydrophobicity to the web's first surface, thereby promoting enhanced effectiveness in transporting fluid away from the first surface of the web, particularly when used in combination with a hydrophilic adhesive applied to the web's second surface in a topsheet system of the present invention.

23 Claims, 2 Drawing Sheets

U.S. PATENT DOCUMENTS

| | | | |
|---|---|---|---|
| 4,820,294 | 4/1989 | Morris | 604/383 |
| 4,839,216 | 6/1989 | Curro et al. | 428/134 |
| 4,921,704 | 5/1990 | Fabo | 424/446 |
| 4,978,436 | 12/1990 | Kelly | 204/165 |
| 5,135,521 | 8/1992 | Luceri et al. | 604/383 |
| 5,169,900 | 12/1992 | Gudelis | 525/106 |
| 5,264,268 | 11/1993 | Luceri et al. | 428/138 |
| 5,288,532 | 2/1994 | Juhl et al. | 428/35.2 |
| 5,334,176 * | 8/1994 | Buenger et al. | 604/374 |
| 5,336,208 * | 8/1994 | Rosenbluth et al. | 604/329 |
| 5,342,334 | 8/1994 | Thompson et al. | 604/366 |
| 5,356,405 * | 10/1994 | Thompson et al. | 604/384 |
| 5,368,910 | 11/1994 | Langdon | 428/137 |
| 5,413,655 | 5/1995 | Nohr et al. | 156/167 |
| 5,476,901 | 12/1995 | Smith et al. | 525/100 |
| 5,514,105 | 5/1996 | Goodman, Jr. et al. | 604/370 |
| 5,685,758 * | 11/1997 | Paul et al. | 442/409 |
| 5,688,259 * | 11/1997 | Osborn, III et al. | 604/385 |
| 5,708,085 * | 1/1998 | Hauenstein et al. | 525/106 |
| 5,792,412 | 8/1998 | Lee et al. | 264/504 |
| 5,885,265 * | 3/1999 | Osborn, III et al. | 604/367 |
| 5,928,210 * | 7/1999 | Ouellette et al. | 604/383 |

* cited by examiner

TOPSHEET SYSTEMS FOR ABSORBENT ARTICLES EXHIBITING IMPROVED HYDROPHILICITY GRADIENTS

FIELD OF THE INVENTION

The present invention relates to topsheet systems for absorbent articles, such as feminine hygiene products, employing hydrophilicity gradients for enhanced fluid handling performance. More particularly, the present invention relates to topsheet systems which exhibit hydrophilicity gradients which are sustainable under in-use conditions and which may be readily and efficiently manufactured.

BACKGROUND OF THE INVENTION

It has long been known in the field of disposable absorbent articles that it is extremely desirable to construct absorptive devices, such as disposable diapers, sanitary napkins, incontinent briefs, bandages, wound dressings, and the like, which are highly effective in receiving and containing urine, menses, and other body exudates. Accordingly, it is generally desirable to promote rapid fluid transfer in a direction away from the wearer and into a retentive structure, while resisting fluid transfer in the reverse direction either toward the wearer or toward external garments or surfaces.

One viable prior art solution to the former problem has been to utilize a covering or topsheet on the exposed, wearer-contacting surface which comprises a web of formed, apertured thermoplastic film. Commonly assigned U.S. Pat. No. 4,342,314, issued to Radel et al. on Aug. 3, 1982, the disclosure of which is hereby incorporated herein by reference, discloses a representative formed film of this variety. Such webs utilize capillary fluid transport to conduct fluid away from one surface (wearer-contacting) into and through the web via three-dimensional capillaries formed into the material, and then into the underlying absorbent structure. In order to address consumer concerns with regard to plastic-like appearance and feel, webs of this variety have been developed which include an interconnected structure of fiber-like appearance in the interest of generating a more cloth-like, aesthetically-pleasing appearance. In addition, apertured, formed thermoplastic film webs have been developed which further include microscopic surface texturing (microtexture) and/or microscopic apertures (microapertures) to further enhance the visual and tactile impression of such webs. Representative film webs of this variety are discloses in commonly assigned U.S. Pat. No. 4,463,045, issued to Ahr et al. on Jul. 31, 1984, and U.S. Pat. No. 4,629,643, issued Dec. 16, 1986 to Curro et al., the disclosures of which are hereby incorporated herein by reference.

While capillary webs of the foregoing varieties are effective in transporting fluid, their effectiveness is limited in that such capillary structures can only move fluid once it reaches the capillary interior. Fluid which wets and remains on wearer contacting surfaces contributes to a "wet" tactile feeling or impression, and to the extent that such fluid may be colored or opaque also contributes to a "stained" visual impression. Surface textures naturally occurring in the material of the web or imparted thereto in formation further increase the likelihood that residual fluid will be trapped or retained on the wearer-contacting surface rather than entering capillary structures for transport away from the surface. Thus, surface topographies which contribute to desirable visual and tactile impressions when dry can also tend to retain residual fluid on the exposed surface and thus reduced desirability under in-use conditions.

Various approaches in the art have attempted to address these issues, including the use of topically-applied hydrophobic surface treatments on the wearer-contacting surface of such webs and surfactants contained within or topically applied to such webs on the garment-facing side of such webs. However, the topical application of such materials to three-dimensional polymeric webs presents certain processing challenges in order to obtain the desired level and orientation of the applied material to achieve the desired level of fluid handling performance.

Accordingly, it would be desirable to provide a topsheet system with enhanced effectiveness in transporting fluid away from one surface which is initially contacted by a fluid.

More particularly, it would be desirable to retain visual and tactile properties of webs having fibrous or otherwise textured surfaces while promoting more rapid and more complete fluid transport away from the wearer-contacting surface and into the interior of an associated absorbent article.

More particularly, it would be desirable to provide such a web which provides desirable visual and tactile characteristics and which may be readily and economically produced.

SUMMARY OF THE INVENTION

The present invention relates to an apertured polymeric film web having a first surface, a second surface generally parallel to and spaced apart from said first surface, and a plurality of fluid passageways extending between the first surface and the second surface to place the first surface and the second surface in fluid communication with one another. The web is formed of a polymeric film comprising at least one bulk modified layer, the bulk modified layer comprising a substantially homogeneous, stabilized dispersion comprising a comparatively low surface energy material in a polymeric material. The comparatively low surface energy material, referred to herein as a hydrophobic additive, imparts hydrophobicity to the web's first surface, thereby promoting enhanced effectiveness in transporting fluid away from the first surface of the web, particularly when used in combination with a hydrophilic adhesive applied to the web's second surface in a topsheet system of the present invention.

In a preferred embodiment the web is used as a topsheet in an absorbent article. In a more preferred embodiment, the web is used as a topsheet in an absorbent article, and the topsheet further includes a hydrophilic adhesive deposited thereon. When used as a topsheet in an absorbent article, the topsheet is peripherally joined with a backsheet and an absorbent core is positioned between the second surface of the topsheet and the backsheet. The second surface of the topsheet is preferably joined to the absorbent core by the hydrophilic adhesive.

BRIEF DESCRIPTION OF THE DRAWINGS

While the specification concludes with claims particularly pointing out and distinctly claiming the present invention, it is believed that the present invention will be better understood from the following description in conjunction with the accompanying drawings, in which like reference numbers identify like elements, and wherein:

DETAILED DESCRIPTION OF THE PRESENT INVENTION

Figure 1:
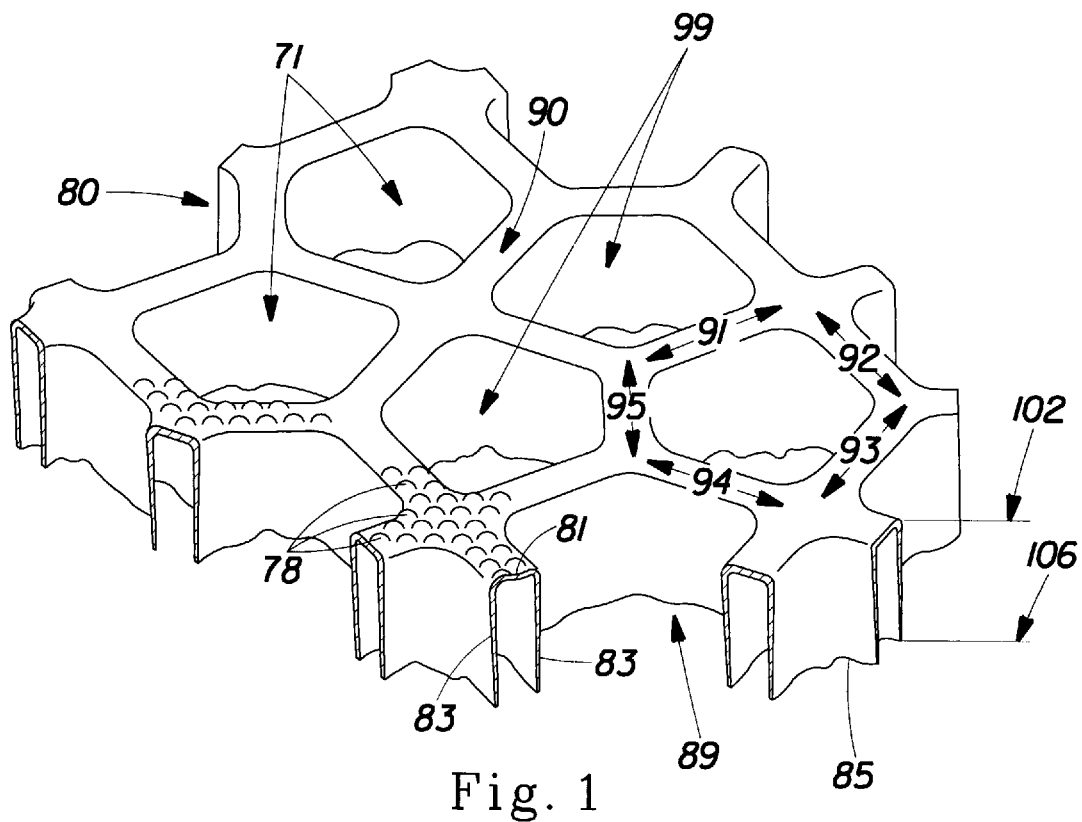
FIG. 1 is an enlarged, partially segmented perspective illustration of a macroscopically expanded, microscopically apertured three-dimensional plastic web of the type generally disclosed in U.S. Pat. No. 4,629,643 constructed in accordance with present invention.
Figure 3:
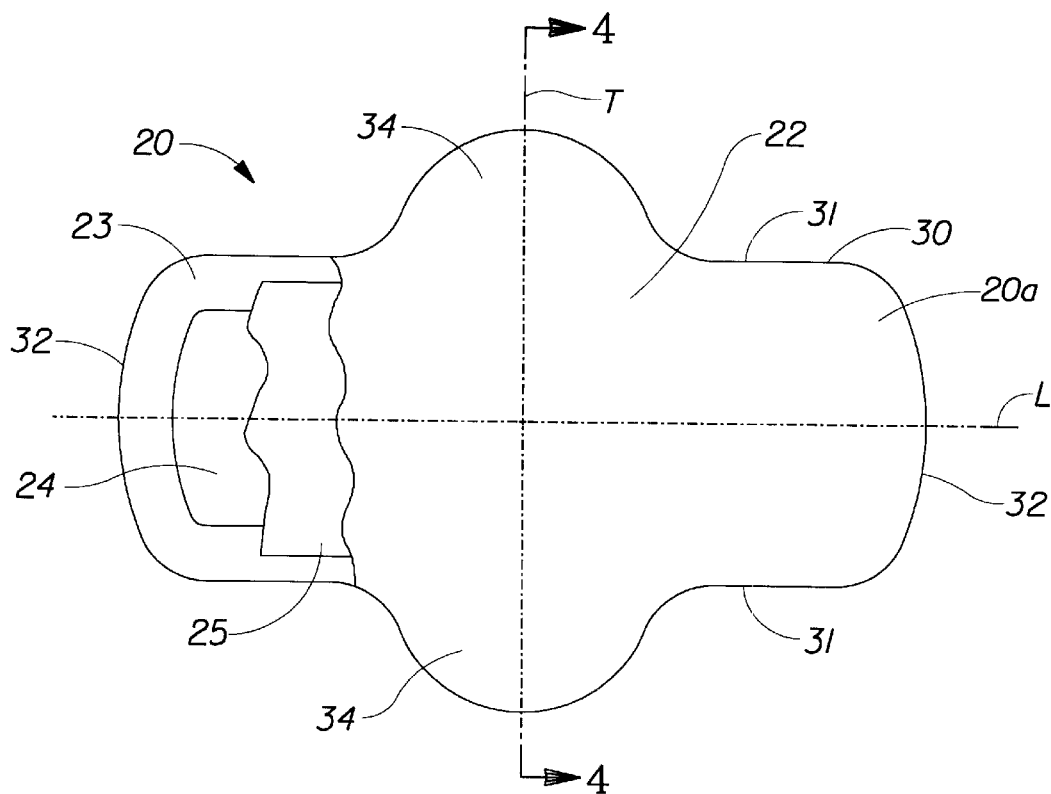
FIG. 3 is a top plan view of a sanitary napkin with portions of the sanitary napkin cut away to more clearly show the construction of the sanitary napkin.
Figure 4:
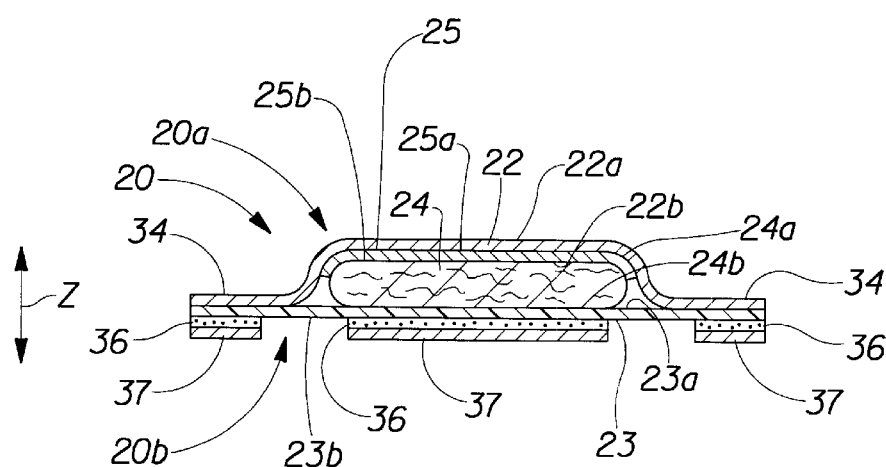
FIG. 4 is a cross-sectional view of the sanitary napkin of FIG. 3 taken along section line 4—4.

FIG. 1 is an enlarged partially segmented, perspective illustration of a three-dimensional, fiber-like, fluid-pervious formed-film web embodiment of the present invention, generally indicated as 80, which has been found highly suitable for use as a topsheet in disposable absorbent articles, such as a sanitary napkin topsheet 22 in a sanitary napkin 20 of the type generally illustrated in FIGS. 3 and 4. The geometrical configuration of the fluid pervious web 80 is generally in accordance with the teachings of the aforementioned '643 Curro et al. patent. Other suitable formed films are described in commonly-assigned U.S. Pat. No. : 3,929,135, issued to Thompson on Dec. U.S. Pat. No. 30, 1975; 4,324,246 issued to Mullane, et al. on Apr. 13, 1982; U.S. Pat. No. 4,342,314, issued to Radel et al. on Aug. 3, 1982; U.S. Pat. No. 4,463,045, issued to Ahr et al. on Jul. 31, 1984; and U.S. Pat. No. 5,006,394 issued to Baird on Apr. 9, 1991. The disclosures of each of these patents are hereby incorporated herein by reference.

The apertured polymeric film webs of the present invention comprise a film in the form of a dispersion comprising a comparatively low surface energy material (hereinafter referred to as a "hydrophobic additive") in a polymeric material. Examples of suitable polymeric materials include but are not limited to polyolefins such as polyethylenes, including linear low density polyethylene, low density polyethylene, ultra low density polyethylene, high density polyethylene, and polypropylene; metallocene catalyst-based polymers; nylon (polyamide); cellulose esters; poly (methyl methacrylate); polystyrene; poly (vinyl chloride); polyester; polyurethane; compatible polymers; compatible co-polymers; biodegradable polymers; and blends, laminates and/or combinations thereof. Films made from such materials may be plasticized with suitable additives known in the art. Other additives may be added to achieve the desired physical characteristics of the web.

The term "fiber-like", as utilized herein to describe the appearance of plastic webs, refers generally to any fine scale pattern of embossments or apertures, random or non-random, reticulated or non-reticulated, which can provide an overall appearance and impression of a woven or nonwoven fibrous web when viewed by the human eye. When describing the elements used to form the web, the term "fiber-like" is utilized herein to describe the appearance or shape of the elements. As utilized herein, the term "macroscopically expanded", when used to describe three-dimensional plastic webs, ribbons and films, refers to webs, ribbons and films which have been caused to conform to the surface of a three-dimensional forming structure so that both surfaces thereof exhibit the three-dimensional pattern of said forming structure, said pattern being readily visible to a normal human eye when the perpendicular distance between the viewer's eye and the plane of the web is about 12 inches.

In general, as utilized herein, the term "macroscopic" is used to refer to structural features or elements which are readily visible to a normal human eye when the perpendicular distance between the viewer's eye and the plane of the web is about 12 inches. Conversely, the term "microscopic" is utilized to refer to structural features or elements which are not readily visible to a normal human eye when the perpendicular distance between the viewer's eye and the plane of the web is about 12 inches.

Such macroscopically expanded webs, ribbons and films are typically caused to conform to the surface of the forming structures by embossing (i.e., when the forming structure exhibits a pattern comprised primarily of male projections), by debossing (i.e., when the forming structure exhibits a pattern comprised primarily of female capillary networks), or by extrusion of a resinous melt onto the surface of a forming structure of either type. By way of contrast, the term "planar" when utilized herein to describe plastic webs, ribbons and films, refers to the overall general condition of the web, ribbon and film when viewed by the naked eye on a macroscopic scale.

The fluid pervious plastic web 80 exhibits a multiplicity of apertures or fluid passageways (e.g., apertures 71) which are formed by a multiplicity of intersecting fiber-like elements (e.g., elements 91, 92, 93, 94, and 95) interconnected to one another in the first or wearer-contacting surface 90 of the web. Each fiber-like element comprises a base portion (e.g., base portion 81) located in plane 102, and each base portion has a sidewall portion (e.g., sidewall portions 83) attached to each edge thereof. The sidewall or intermediate portions 83 extend generally in the direction of the second surface 85 of the web. The intersecting sidewall portions of the fiber-like elements are interconnected to one another intermediate the first and second surfaces of the web, and terminate substantially concurrently with one another in the plane 106 of the second surface 85.

As utilized herein, the term "fluid passageway" is intended to encompass enclosed or at least partially enclosed structures or channels which may communicate fluids. The term fluid passageway is thus intended to encompass the terms "aperture", "channel", "capillary", as well as other similar terms. Although in FIG. 1 the fluid passageways are depicted in the form of interlocking polygonal shapes, fluid passageways incorporated into topsheet systems in accordance with the present invention may be of any desired cross-sectional shape such as circular, elliptical, teardrop, or other geometrical shapes as desired for any particular application.

In a particularly preferred embodiment, the interconnected sidewall or intermediate portions 83 terminate substantially concurrently with one another in the plane 106 of the second surface 85 to form apertures 89 in the second surface 85 of the web. The capillary networks 99 formed by the interconnected sidewall or intermediate portions 83 allow for the free transfer of fluid from the first or wearer-contacting surface 90 of the web directly to the second surface 85 of the web without lateral transmission of fluid between adjacent capillary networks.

Each of the fiber-like elements exhibits a substantially uniform U-shaped cross-section along its length. In the case of a primary fiber-like element, its cross-section comprises a base portion located in the wearer-contacting plane and a sidewall portion joined to each edge of the base portion and extending generally in the direction of the absorbent pad-contacting surface of the web. The sidewall portions which intersect one another are joined to one another intermediate the wearer-contacting surface and the absorbent pad-contacting surface of the web, thereby forming a capillary network interconnecting the opposed surfaces of the web.

Webs of this construction have been utilized with success as topsheets in absorbent articles such as catamenial pads, most commonly when rendered at least somewhat wettable through the use of various wettability-enhancing surfactants (applied during extrusion or topically as a secondary step after film manufacture). However, in accordance with the present invention the wettability of such webs is reduced below that typically exhibited by the polymeric material itself through the use of wettability-reducing components, i.e., hydrophobic additives, in the polymeric resin. A relatively hydrophobic web of the present invention may be part of a topsheet system, the system further comprising materials having diverse surface energy (hydrophobicity/hydrophilicity) characteristics, thereby providing a surface energy gradient for facilitating desired fluid movement.

Figure 2:
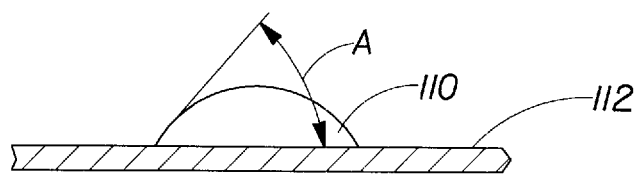
FIG. 2 is an enlarged cross-sectional view of a droplet of liquid on a solid surface, where angle A illustrates the contact angle of the liquid with the solid surface.

A useful parameter of wettability is the contact angle that a drop of liquid (gas-liquid interface) makes with the solid surface (gas-solid interface). Typically, as shown in FIG. 2, a drop of liquid 110 placed on a solid surface 112 makes a contact angle, A, with the solid surface, as seen in FIG. 2. As the wettability of the solid surface by the liquid increases, the contact angle, A, decreases. As the wettability of the solid surface by the liquid decreases, the contact angle, A, increases. The liquid-solid contact angle may be determined from techniques known in the art, such as those described in greater detail in *Physical Chemistry of Surfaces*, Second Edition, by Arthur W. Adamson (1967), F. E. Bartell and H. H. Zuidema, *J. Am. Chem. Soc.*, 58, 1449 (1936), and J. J. Bikerman, *Ind. Eng. Chem. Anal. Ed.*, 13, 443 (1941), each of which are hereby incorporated herein by reference. More recent publications in this area include Cheng, et al., *Colloids and Surfaces* 43:151–167 (1990), and Rotenberg, et al., *Journal of Colloid and Interface Science* 93(1):169–183 (1983), which are also hereby incorporated herein by reference.

As used herein, the term "hydrophilic" is used to refer to surfaces that are wettable by aqueous fluids (e.g., aqueous body fluids) deposited thereon. Hydrophilicity and wettability are typically defined in terms of contact angle and the surface tension of the fluids and solid surfaces involved. This is discussed in detail in the American Chemical Society publication entitled *Contact Angle, Wettability and Adhesion*, edited by Robert F. Gould (Copyright 1964), which is hereby incorporated herein by reference. A surface is said to be wetted by a fluid (hydrophilic) when the fluid tends to spread spontaneously across the surface. Conversely, a surface is considered to be "hydrophobic" if the fluid does not tend to spread spontaneously across the surface.

The contact angle depends on surface inhomogeneities (e.g., chemical and physical properties, such as roughness), contamination, chemical/physical treatment of or composition of the solid surface, as well as the nature of the liquid and its contamination. There is also an inverse relationship between contact angle and surface energy such that as the surface energy of the solid decreases, the contact angle increases. Accordingly, as surface energy decreases, fluid in contact with the surface tends to "bead up" and occupy a smaller surface area of contact. The reverse is likewise true as the surface energy increases with a given fluid. Surface energy, therefore, influences interfacial fluid phenomena on the solid surface. Therefore, one measure of surface energy is the contact angle a drop of a given fluid makes with the surface.

One benefit to having a topsheet with a comparatively low surface energy in accordance with the aforementioned description is the reduced potential for rewet. As use forces tend to force the collected fluid to rewet or be squeezed out of the pad (e.g., squeezed by compression from the absorbent core towards the first surface of the topsheet), such undesirable movement will be resisted by the first surface of the topsheet which has a relatively low surface energy to repel the fluid as it attempts to make its way out of the pad through the openings in the topsheet.

While many structures in the prior art have attempted to utilize various superficial coatings to impart greater hydrophobicity and/or reduced coefficient of friction to the overall upper surface of a web, such coatings typically substantially reduce if not eliminate topographical surface features present in the uncoated web. As discussed above, such surface features are an important physical feature with regard to visual and tactile impression. Moreover, such coatings on relatively planar substrates typically have a smooth, glossy finish which accentuates the sweaty, sticky, plastic-like feel of such webs.

Without wishing to be bound by theory, surface topography is believed to play a major role in not only reducing the negative visual and tactile impressions normally associated with such webs, but also in the handling and/or transport and retention of bodily fluids. Accordingly, fluid pervious webs according to the present invention preferably are constructed so as to preserve the physical surface topography of the initially formed web, i.e., wherein the surface features are not compromised in the process of imparting enhanced hydrophobicity to the web.

By way of a representative illustration of the synergism of the present invention vis-a-vis the combination or superposition of capillary (including fluid surface tension) and surface energy effects, capillary webs according to the present invention have been found to exhibit a unique combination of properties viewed as important from a consumer perspective. More particularly, capillary webs according to the present invention have been found to exhibit good acquisition, dryness, and masking characteristics.

In general, acquisition is a reflection of the degree to which the fluid transport web does or does not interfere with fluid pass-through. Improved acquisition rates/times, as determined by gush acquisition tests, reflect little interference or impedance of fluid pass-through, as well as actual influence of fluid driving forces such as capillarity and surface energy gradients. Dryness is a reflection of the degree to which the fluid transport structure: (1) successfully passes fluid through its plane (without retention); and (2) resists fluid transport in the opposite direction, in essence, the degree to which the structure acts as a one-way valve for fluid flow in a preferential direction. Improved topsheet dryness, as determined by product rewet tests, contributes to overall wearer comfort and cleanliness. Masking reflects the cleanliness of the surface after fluid pass-through, further defined as the degree of coloration remaining (with a colored fluid) as well as the size or extend of the discolored region.

Typically, as the surface energy of a given capillary web structure decreases uniformly the masking and dryness at the surface improve, but at the expense of a reduction in acquisition characteristics. Conversely, improvements in acquisition realized by a uniform increase in surface energy of a given capillary web structure are typically offset by reduced masking and dryness characteristics. By utilizing the surface energy/surface tension principles of the present invention, increases in dryness and/or masking characteristics may be obtained without sacrifices in the remaining parameters, such as acquisition rates. In a preferred embodiment, the surface energy of the upper (body-facing) surface of an apertured polymeric film is decreased below levels exhibited by current materials utilized to form fluid pervious webs. In addition, in a most preferred embodiment, the surface tension of the fluid being transferred through the apertured film is reduced, further enhancing the fluid transfer characteristics of the film.

In addition to the surface energy of the material (which depends upon the composition of the materials utilized), porosity or capillary size, and fluid surface tension, a number of other physical parameters should be considered in designing a web according to the present invention for proper fluid handling. Such factors include the diffusion properties of materials, bio-compatibility of materials, overall web caliper and geometry, surface topography, fluid viscosity, and the presence or absence of other structures on either side of the web.

In order to provide the porous polymeric webs of the present invention with reduced wettability (enhanced hydrophobicity), the polymeric materials from which they are made are blended with hydrophobic additives which reduce the surface energy of the polymer on a bulk basis, known in the art as "bulk modification". Said differently, the use of a comparatively low surface energy materials, such as silicones or fluoropolymers, as a hydrophobic additive at a relatively low add-on level is utilized to impart its beneficial surface energy properties to the bulk polymeric material utilized to form the finished web.

The ultimate goal of "bulk modification" is based on the design of a polymer of specific surface composition from the knowledge of the surface related phenomena on multi-component polymeric systems. In this case, "multi-component polymeric system" refers to materials made by macromolecular chains whose repeating unit is different (such as blends) or by macromolecules containing blocks of different repeating units in the same chain (block copolymers).

When adding hydrophobic additives to a polymeric resin material, i.e., a polymeric material prior to web formation, the relative compatibility or incompatibility of the two materials is an important factor in determining the resulting properties of the overall web. When the two materials are relatively compatible with one another they will tend to combine and/or react with one another to form a new homogeneous material having new properties compared with those of the constituent materials. On the other hand, where the two materials are relatively incompatible with one another they will tend to separate from one another and coalesce with molecules of their own kind to form a two-phase two-element material. Depending upon such factors as surface energy, molecular weight, relative proportions, and the like the two materials may separate into a side-by-side relationship or with one material surrounding the other material to form a skin layer or shell.

Under the right conditions a result between these two extremes may be realized, i.e., a dispersion (or an emulsion if the components are in liquid form) with comparatively small concentrations of one component homogeneously dispersed within the other component may be formed. To achieve such a dispersion, the compatibility of the constituents must be balanced so as to prevent separation and coalescence as well as combination of the elements. Even once such a condition is attained, in many instances the homogeneity is but a temporary condition which lacks sufficient stability pending crystallization to fix the homogeneous distribution of the dispersed hydrophobic additive.

In accordance with the present invention, a suitable hydrophobic additive is a material having a comparatively low surface energy that can be incorporated into the polymeric resin while in melt form to form a two-phase stabilized dispersion of the two materials. Upon crystallization, a stable dispersion will be formed. As used herein, the terms "stabilized" and "stable" refer to the relative inability of the hydrophobic additive to readily migrate, or diffuse, to the surface of the material. Stability, in the context of the present invention, is generally related to the molecular weight of the constituent components. For example, a dispersion in which the dispersant is of such a molecular weight that little or no diffusion occurs in the normal life of the product is considered a stabilized dispersion.

A suitable hydrophobic additive preferably has the effect of decreasing the surface energy of the bulk modified film. A presently preferred hydrophobic additive comprises polydimethylsiloxane and other substituted species (referred to as "PDMS" herein) incorporated into the polymeric resin at a level of between about 1.5% and about 5% by weight, the PDMS having a molecular weight of about $1 \times 10^6$. For example, in a two layer film, having a bulk modified skin layer of 0.2 mils coextruded with an unmodified layer of 0.8 mils (total nominal 1.0 mils), the skin layer PDMS loading would be from about 1.5% up to about 5.0%. The corresponding net film PDMS loading would be 0.3% to about 1.2% by weight. A presently preferred polymeric material comprises polyethylene in a blend of linear low density polyethylene (LLDPE) and low density polyethylene (LDPE). The relative molecular weights of PDMS and polyethylenes are such that little or no diffusion occurs in the expected life (i.e., from production to purchase by the user) of products utilizing the web of the present invention. As noted above, therefore, PDMS and polyethylene have been found to form a stabilized dispersion useful for forming low surface energy materials for use in webs of the present invention.

Polydimethylsiloxane is prepared by the hydrolysis of the organochlorosilane monomers into polymers by crosslinking. These resins owe their stability to strong silicon-oxygen-silicon bonds. In the present invention the radical used for crosslinking the monomer is methyl. The repeating structure is of the type:

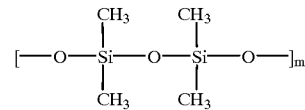

These resins have extremely good thermal stability, excellent insulating properties, and high water repellency (hydrophobicity). A more detailed discussion of such resins may be found in commonly-assigned U.S. Pat. No. 5,476,901, entitled "Siloxane Modified Polyolefin Copolymers", issued Dec. 19, 1995 to Smith et al., the disclosure of which is hereby incorporated herein by reference.

Due to the comparatively high molecular weight of the PDMS it does not tend to "bloom" to the surface, a phenomenon observed with many conventional comparatively lower molecular weight surface active agents (surfactants). Instead, the surface effect of the finished web is imparted by PDMS molecules present at the web surface at the time of crystallization of the polymeric resin material.

The behavior of blends of incompatible polymer resins is described in greater detail in *Polymer Surfaces*, by Fabio Garbassi, Marco Morra, and Ernesto Occhiello (Copyright 1994), which is hereby incorporated herein by reference. Chapter 8 thereof is particularly illustrative of bulk modification behavior of incompatible polymers.

The desired resin composition is obtained by starting with a PDMS masterbatch commercially available from Dow Corning, for example, under either of the trade designations MB050-002, or PE100 additive. This masterbatch comprises PDMS additives blended with low density polyethylene to form pellets. The masterbatch of PDMS is supplied in pellet form with either a 25% or 50% (by weight) concentration of PDMS. The plastic film manufacturer dry blends the PDMS masterbatch with other resin components such as additional LDPE and/or LLDPE to achieve the desired final concentration level within the base polyethylene film, according to the desired single layer, or co-extruded (multi-layer), film format.

The use of bulk modified polymeric resins designed in accordance with the above-described bulk modification principles permits the efficient tailoring of the hydrophobicity properties of the overall polymeric film web utilizing a comparatively small proportion of a concentrated additive. Depending upon the desired properties of the finished web, another approach which may also be utilized in combination with bulk modification is to utilize a multi-layered (bi-layered, A/B) approach wherein the bulk-modified polymer is utilized as a "skin layer" (layer "A") on top of, i.e., by coextrusion, an un-modified polymeric film layer to form a cohesive structure with an exposed surface having the desired properties. In the product context, the "A" layer of the film is on the body-facing surface of the finished web. For example, a multilayer coextruded film utilizing Dow Corning MB050-002 PDMS in a 0.2 mil bulk-modified layer (layer "A") was coextruded with a 0.6 mil un-modified layer (layer "B") to produce a film having an overall film thickness of 0.8 mils. Similar films having an overall thickness of 1.0 mil (0.2 mil bulk modified (Dow Corning PE100)/0.8 mil un-modified) were also produced. Multi-layer films with three (i.e., A/B/A or A/B/C) or more layers may also be produced having bulk-modified polymer layers on one or both exterior surfaces of the film.

By way example of the beneficial decrease in surface energy, and therefore the increase in hydrophobicity, of the surface of a web of the present invention, the change in contact angles between small drops of fluid on the surfaces of an unmodified web and a web of the present invention was measured. Contact angles may be measured by any method known in the art, such as those described in greater detail in the aforementioned *Physical Chemistry of Surfaces*, Second Edition, by Arthur W. Adamson (1967), F. E. Bartell and H. H. Zuidema, *J. Am. Chem. Soc.*, 58, 1449 (1936), and J. J. Bikerman, *Ind. Eng. Chem., Anal. Ed.*, 13, 443 (1941).

The contact angle of water drops having a volume of 1–4 microliters on unmodified polyethylene were compared to the contact angle of same size drops on a multilayer coextruded film of the present invention. In general, a 4 microliter-size drop is adequate for determining contact angles on flat films. A 1 microliter-size drop is preferred for determining contact angles on hydroformed films so that the drop may be placed on flat areas of the film.

In representative contact angle comparison tests using a goniometer, the contact angle of water on a 1.0 mil thick monolayer polyethylene (50/50 LDPE/LLDPE) sheet was determined and compared to the contact angle of water on a 1.0 mil thick multilayer coextruded film as detailed above. In particular, the 0.2 mil bulk-modified skin layer of the multilayer film comprised 1.5% by weight of PE100 PDMS within the skin layer, with the balance polyethylene, and the 0.8 mil unmodified layer comprised polyethylene. The measured contact angle formed on the monolayer sheet was about 90°, while the measured contact angle formed on the bulk-modified layer of the multilayer sheet was about 100–1100°. Similar changes in contact angle were measured using artificial menstrual fluid, with average contact angles increasing from about 81° to about 92°.

A preferred method for converting a web of polymeric film into an apertured formed film of the type depicted in FIG. 1 is by applying a high pressure fluid jet comprised of water or the like against one surface of the as-extruded film, preferably while applying a vacuum adjacent the opposite surface of the film. Such methods are described in greater detail in commonly assigned U.S. Pat No. 4,609,518 issued to Curro et al. on Sep. 2, 1986; U.S. Pat. No. 4,629,643 issued to Curro et al. on Dec. 16, 1986; U.S. Pat. No. 4,637,819 issued to Ouellette et al. on Jan. 20, 1987; U.S. Pat. No. 4,681,793 issued to Linman et al. on Jul. 21, 1987; U.S. Pat. No. 4,695,422 issued to Curro et al. on Sep. 22, 1987; U.S. Pat. No. 4,778,644 issued to Curro et al. on Oct. 18, 1988; U.S. Pat. No. 4,839,216 issued to Curro et al. on June 13, 1989; and U.S. Pat. No. 4,846,821 issued to Lyons et al. on Jul. 11, 1989, the disclosures of each of said patents being incorporated herein by reference.

Hydrophobic additive PDMS is added during film extrusion by the polymeric film manufacturer. The bulk modified polymeric film (or the coextruded multi-layer film having bulk modified skin layer(s)) is quenched (crystallized) following extrusion at the embossing nip, for example by water cooled rolls. This ensures a homogeneous distribution of the minor constituent (PDMS) is maintained in the finished (cured) bulk-modified layer(s). As an alternative formation process, the bulk modified polymeric film (or a coextruded multi-layer film having bulk modified skin layer(s)) may be formed as a flat film (blown, cast, etc.) which is then subjected to heating to soften the film and then the aperture formation process, as also disclosed in the aforementioned Radel et at. patent. Other formation processes known and described in the art, such as those exemplified in the above referenced and incorporated U.S. Patents, may be utilized for forming three-dimensional films, such as vacuum forming, thermoforming, etc.

A co-extruded film format is preferred to a mono-layer (single layer) execution for PDMS usage efficiency. For a nominal 1.0 film total basis weight and a mono-layer format, the PDMS net film loadings would be in the 1.5% to 5.0% by weight range. For a 0.2/0.8 mil layer split of a co-extruded film at the same basis weight, the PDMS net film loading would be about 5X lower or in the 0.3% to 1.0% by weight range. Hence, net PDMS usage is minimized for co-extruded film executions. A three-layer co-extruded film would have greater PDMS efficiency than a two-layer coextruded format. Also, minimization of the skin layer basis weight further improves PDMS usage efficiency. Further, process efficiency and hygiene gains are expected for PDMS in a co-extruded format given less PDMS bleedthrough and contamination of the surfaces (rolls and idlers) which it contacts following extrusion.

Following manufacture of such microapertured formed films, they may be incorporated into absorbent articles such as those depicted in FIGS. 3–4. Indeed, the surface energy properties of the present invention are particularly useful in combating the tendency of fluids to accumulate in and around the microstructures present in formed films such as depicted in FIG. 1. This leads to webs having improved clothlike characteristics without sacrificing apparent consumer dryness.

After the bulk modified polymeric film has been cured and either before or after the film has been apertured and/or macroscopically expanded as described above, the film may be subjected to post-formation mechanical, chemical, or other treatments to obtain the desired properties in the finished web. For example, the film may be embossed, strained, or otherwise deformed or such treatments as topical surfactant application and corona discharge treatment may be applied as desired.

In accordance with the present invention, to produce an even greater surface energy gradient, bulk-modified, apertured, polymeric film webs are utilized in combination with other materials having diverse surface energy (hydrophobicity/hydrophilicity) characteristics in the construction of certain articles, particularly disposable absorbent articles such as those described hereafter, to provide a synergistic topsheet system. In a preferred configuration, the film web is utilized as a topsheet on an absorbent article with a hydrophilic adhesive applied to the second or garment facing surface of the film such that it is disposed between the apertured polymeric film web and an underlying absorbent element such as a secondary topsheet or layer of the absorbent core. Examples of hydrophilic adhesives suitable for such use include hydrophilic hot melt adhesives with a resin incorporated surfactant such as HX-4111-01 manufactured by Findlay Adhesives of Minneapolis, Minn.

Such adhesives may be applied utilizing techniques conventional in the art for such applications, including a uniform continuous layer of adhesive, a patterned layer of adhesive or any array of separate lines, spirals or spots of adhesive. In a preferred configuration, the hydrophilic adhesive is applied to the second or garment-facing surface of the polymeric film web and then secured to an underlying acquisition layer or secondary topsheet of the absorbent article. This approach provides for a desired level of control over the ultimate location and disposition of the hydrophilic adhesive with respect to the lower ends of the fluid passageways in the second surface of the web, such that the fluid entering into the fluid passageways experiences a driving force away from the wearer-contacting surface and toward the absorbent core as described above. Alternatively, the hydrophilic adhesive may be applied to the wearer-facing surface of such an underlying layer such that it will directly and intimately contact the second or garment-facing surface of the polymeric film web once the components of the absorbent article are assembled.

When used with a web in a topsheet system of the present invention, the hydrophilic adhesive is beneficial in increasing fluid flow by at least two mechanisms. For one, due to its high surface energy, the adhesive helps create a driving force which facilitates the movement of fluid across the boundary between the highly hydrophobic polymeric film on the body-facing surface of the web to the absorbent layer adjacent to the garment facing surface of the web, thereby improving the fluid handling performance of such absorbent articles. Therefore, fluid transfer, e.g., fluid acquisition, from the body-facing surface of the topsheet to the garment-facing side of the topsheet is enhanced by differences in the respective surface energies. However, fluid movement, in particular drainage from fluid capillaries in a hydroformed topsheet, is also enhanced by a second mechanism, namely a change in the surface tension of the fluid due to the presence of surfactant in the hydrophilic adhesive. The surfactant gets transferred via contact into the moving fluid front to reduce the fluid's surface tension, thereby increasing the propensity of the fluid to wet the second, garment-facing surface of the web. By adjusting the level of adhesive used, the level of wettability can be balanced with other web fluid handling characteristics so as not to negatively impact topsheet rewet properties.

Another advantage of using the hydrophilic adhesive to provide a hydrophilic character to the garment-facing (second) surface of the hydrophobic, bulk-modified polymeric film material, is that it is comparatively more resistant to migration, diffusion, and contamination effects than topical applications of surfactant solutions after production of the film material. Moreover, the controlled application of the hydrophilic adhesive allows greater control over the ultimate disposition of the hydrophilic treatment vis-à-vis the application of the treatment to the lower ends of the fluid passageways or capillaries. When utilized in combination with a film material which is hydroformed via a pressurized stream of aqueous fluid, this approach also avoids the issue of surfactant loss which occurs when a resin-incorporated surfactant system is utilized with a surfactant incorporated throughout the polymeric resin prior to the formation process.

To measure the surface tension change of fluids contacting the hydrophilic adhesive, individual 5 cm×5 cm samples of web treated with the aforementioned HX-4111-01 adhesive were placed in a vial to which 20 mL of water were added. Each sample was soaked for five minutes, at which time the sample was removed and the surface tension of the remaining water was measured using a Fischer Model 21 tensionmeter at room temperature. The surface tension of distilled water is generally about 72 dyne/cm. When tested by the method above, the surface tension of water dropped to as low as 53 dyne/cm, depending on the amount of adhesive present in the system. This reduction in fluid surface tension, combined with surface energy effects of the topsheet system, produces superior fluid-handling capability, including faster acquisition, and less rewet, resulting in a dryer, more comfortable topsheet for an absorbent article.

It has been found that the level of hydrophilic adhesive, and the level of surfactant it contains, if any, plays a large roll in the fluid handling properties of the topsheet system of the present invention. In general, it has been found that increasing the amount of HX-4111-01, for example, to levels above about 2 mg/sq.in. tends to lower the gush acquisition time, but tends to increase the rewet amount. A preferred balance is achieved by applying the adhesive by fibrillization at about 1–2 mg/sq.in. However, different adhesives with different secondary topsheet/absorbent core systems may require adjustments in the level of adhesive to achieve desired results.

It is noted that these numbers are general in nature, and may be influenced by other parameters such as adhesive type and method of application, contact area between the film topsheet and secondary topsheet, and any subsequent absorbent layers used in combination with the topsheet system disclosed. In particular, tertiary topsheets and additional surfactants have been found to have a significant impact on topsheet system performance. Therefore, the data presented by way of example is to be exemplary and not limiting.

REPRESENTATIVE ABSORBENT ARTICLE

As used herein, the term "absorbent article" refers generally to devices used to absorb and contain body exudates, and more specifically refers to devices which are placed against or in proximity to the body of the wearer to absorb and contain the various exudates discharged from the body. The term "absorbent article" is intended to include diapers, catamenial pads, tampons, sanitary napkins, incontinence pads, and the like, as well as bandages and wound dressings. The term "disposable" is used herein to describe absorbent articles which are not intended to be laundered or otherwise restored or reused as an absorbent article (i.e., they are intended to be discarded after limited use, and, preferably, to be recycled, composted or otherwise disposed of in an environmentally compatible manner). A "unitary" absorbent article refers to absorbent articles which are formed as a single structure or as separate parts united together to form a coordinated entity so that they do not require separate manipulative parts such as a separate holder and pad.

A preferred embodiment of a unitary disposable absorbent article made in accordance herewith is the catamenial pad, sanitary napkin 20, shown in FIG. 3. As used herein, the term "sanitary napkin" refers to an absorbent article which is worn by females adjacent to the pudendal region, generally external to the urogenital region, and which is intended to absorb and contain menstrual fluids and other vaginal discharges from the wearer's body (e.g., blood, menses, and urine). Interlabial devices which reside partially within and partially external to the wearer's vestibule are also within the scope of this invention. It should be understood, however, that the present invention is also applicable to other feminine hygiene or catamenial pads, or other absorbent articles such as diapers, incontinent pads, and the like, as well as other webs designed to facilitate fluid transport away from a surface such as disposable towels, facial tissues, and the like.

It is to be understood that the overall size, shape, and/or configuration of the absorbent article, if any, into which porous polymeric webs according to the present invention are incorporated, or utilized in conjunction with, have no criticality or functional relationship to the principles of the present invention. Such parameters, however, must be considered along with the intended fluid and intended functionality when determining appropriate web configurations and compositions according to the present invention.

Sanitary napkin 20 is illustrated as having two surfaces such as first surface 20a, sometimes referred to as a wearer-contacting or facing surface, a body-contacting or facing surface or "body surface", and second surface 20b, sometimes referred to as a garment-facing or contacting surface, or "garment surface". The sanitary napkin 20 is shown in FIG. 3 as viewed from its first surface 20a. The first surface 20a is intended to be worn adjacent to the body of the wearer. The second surface 20b of the sanitary napkin 20 (shown in FIG. 4) is on the opposite side and is intended to be placed adjacent to the wearer's undergarment when the sanitary napkin 20 is worn.

The sanitary napkin 20 has two centerlines, a longitudinal centerline "L" and a transverse centerline "T". The term "longitudinal", as used herein, refers to a line, axis or direction in the plane of the sanitary napkin 20 that is generally aligned with (e.g., approximately parallel to) a vertical plane which bisects a standing wearer into left and right body halves when the sanitary napkin 20 is worn. The terms "transverse" or "lateral" as used herein, are interchangeable and refer to a line, axis or direction which lies within the plane of the sanitary napkin 20 that it generally perpendicular to the longitudinal direction. FIG. 3 also shows that the sanitary napkin 20 has a periphery 30 which is defined by the outer edges of the sanitary napkin 20 in which the longitudinal edges (or "side edges") are designated 31 and the end edges (or "ends") are designated 32.

FIG. 3 is top plan view of a sanitary napkin 20 of the present invention in a substantially flat state with portions of the sanitary napkin being cut away to more clearly show the construction of the sanitary napkin 20 and with the portion of the sanitary napkin 20 which faces or contacts the wearer 20a oriented towards the viewer. As shown in FIG. 3, the sanitary napkin 20 preferably comprises a liquid pervious topsheet 22, a liquid impervious backsheet 23 joined with the topsheet 22, an absorbent core 24 positioned between the topsheet 22 and the backsheet 23, and a secondary topsheet or acquisition layer 25 positioned between the topsheet 22 and the absorbent core 24. In the representative absorbent article of FIGS. 3 and 4, the topsheet 22 comprises a porous polymeric web in accordance with the present invention (such as depicted in FIG. 1).

The sanitary napkin 20 preferably includes optional side flaps or "wings" 34 that are folded around the crotch portion of the wearer's panty. The side flaps 34 can serve a number of purposes, including, but not limited to helping to hold the napkin in proper position while protecting the wearer's panty from soiling and keeping the sanitary napkin secured to the wearer's panty.

FIG. 4 is a cross-sectional view of the sanitary napkin 20 taken along section line 4—4 of FIG. 3. As can be seen in FIG. 4, the sanitary napkin 20 preferably includes an adhesive fastening means 36 for attaching the sanitary napkin 20 to the undergarment of the wearer. Removable release liners 37 cover the adhesive fastening means 36 to keep the adhesive from sticking to a surface other than the crotch portion of the undergarment prior to use.

The topsheet 22 has a first surface 22a and a second surface 22b positioned adjacent to and preferably secured to a first surface 25a of the fluid acquisition layer to promote fluid transport from the topsheet to the acquisition layer. The second surface 25b of the acquisition layer 25 is positioned adjacent to and is preferably secured to the first surface 24a of an absorbent core or fluid storage layer 24 to promote fluid transport from the acquisition layer to the absorbent core. The second surface 24b of the absorbent core 24 is positioned adjacent to and is preferably secured to the first surface 23a of the backsheet 23.

In addition to having a longitudinal direction and a transverse direction, the sanitary napkin 20 also has a "Z" direction or axis, which is the direction proceeding downwardly through the topsheet 22 and into whatever fluid storage layer or core 24 that may be provided. The objective is to provide a substantially continuous path between the topsheet 22 and the underlying layer or layers of the absorbent article herein, such that fluid is drawn in the "Z" direction and away from the topsheet of the article and toward its ultimate storage layer.

The absorbent core 24 may be any absorbent means which is capable of absorbing or retaining liquids (e.g., menses and/or urine). As shown in FIGS. 3 and 4, the absorbent core 24 has a body surface 23a, a garment facing surface 24b side edges, and end edges. The absorbent core 24 may be manufactured in a wide variety of sizes and shapes (e.g. rectangular, oval, hourglass, dogbone, asymmetric, etc.) and from a wide variety of liquid-absorbent materials commonly used in sanitary napkins and other absorbent articles such as communitive wood pulp which is generally referred to as airfelt. Examples of other suitable absorbent materials include creped cellulose wadding; meltblown polymers including coform; chemically stiffened, modified or cross-linked cellulosic fibers; synthetic fibers such as crimped polyester fibers; peat moss; tissue including tissue wraps and tissue laminates; absorbent foams; absorbent sponges; superabsorbent polymers; absorbent gelling materials; or any equivalent material or combination of materials, or mixtures of these.

The configuration and construction of the absorbent core may also be varied (e.g., the absorbent core may have varying caliper zones (e.g. profiled so as to be thicker in the center), hydrophilic gradients, superabsorbent gradients or lower density or lower average basis weight acquisition zones; or may comprise one or more layers or structures). The total absorbent capacity of the absorbent core, should, however, be compatible with the design loading and the intended use of the absorbent article. Further, the size and absorbent capacity of the absorbent core may be varied to accommodate different uses such as incontinent pads, pantiliners, regular sanitary napkins, or overnight sanitary napkins.

Exemplary absorbent structures for use as the absorbent core in the present invention are described in U.S. Pat. No. 4,950,264 issued to Osborn on Aug. 21, 1990; U.S. Pat. No. 4,610,678 issued to Weisman et al. on Sep. 9, 1986; U.S. Pat. No. 4,834,735 issued to Alemany et al. on May 30, 1989; and European Patent Application No. 0 198 683, the Procter & Gamble Company, published Oct. 22, 1986 in the name Duenk, et al. The disclosures of each of these patents are incorporated herein by reference.

The backsheet 23 and the topsheet 22 are positioned adjacent the garment facing surface and the body facing surface respectively of the absorbent core 24 and are preferably joined thereto and to each other by attachment means (not shown) such as those well known in the art. For example, the backsheet 23 and/or the topsheet 22 may be secured to the absorbent core or to each other by a uniform continuous layer of adhesive, a patterned layer of adhesive or any array of separate lines, spirals or spots of adhesive. Adhesives which have been found to be satisfactory are manufactured by H.B. Fuller Company of St. Paul, Minn. under the designation HL-1258, and by Findlay of Minneapolis, Minn., under the designation H-2031. Adhesives which have been found to be suitable for use as hydrophilic adhesives in accordance with the present invention adhesives with a resin incorporated surfactant manufactured by Findlay of Minneapolis, Minn., under the designation HX-4111-01. The attachment means will preferably comprise an open pattern network of filaments of adhesive as disclosed in U.S. Pat. No. 4,573,986 issued to Minetola et al. on Mar. 4, 1986, the disclosure of which is incorporated herein by reference. An exemplary attachment means of an open patterned network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zieker, et al. on Nov. 22, 1978 and U.S. Pat. No. 4,842,666 issued to Werenicz on Jun. 27, 1989. The disclosures of each of these patents are incorporated herein by reference. Alternatively, the attachment means may optionally comprise heat bonds, pressure bonds, ultrasonic bonds, dynamic mechanical bonds or any other suitable attachment means or combinations of these attachment means as are known in the art.

The backsheet 23 is impervious to liquids (e.g., menses and/or urine) and is preferably manufactured from flexible liquid impervious materials such as thin plastic film. As used herein, the term "flexible" refers to materials which are compliant and are more readily conformed to the general shape and contours of the human body.

The backsheet 23 prevents the exudates absorbed and contained in the absorbent core from wetting articles which contact the sanitary napkin 20 such as pants, pajamas and undergarments. The backsheet 23 may comprise a woven or nonwoven material, polymeric films such as thermoplastic films of polyethylene or polypropylene, or composite materials such as a film-coated nonwoven material. The backsheet may be constructed of a polyethylene film having a thickness of from about 0.012 mm (0.5 mil) to about 0.051 mm (2.0 mil). Exemplary polyethylene films are manufactured by Clopay Corporation of Cincinnati, Ohio, under the designation P18-1401 and by Tredegar Film Products of Terre Haute, Ind., under the designation XP-9818. The backsheet is preferably embossed and/or matte finished to provide a more clothlike appearance. Further, the backsheet 23 may permit vapors to escape from the absorbent core 24 (i.e., breathable) while still preventing exudates from passing through the backsheet 23.

In use, the sanitary napkin 20 can be held in place by any support means or attachment means (not shown) well-known for such purposes. Preferably, the sanitary napkin is placed in the user's undergarment or panty and secured thereto by a fastener such as an adhesive. The adhesive provides a means for securing the sanitary napkin in the crotch portion of the panty. Thus, a portion or all of the outer or garment facing surface 23b of the backsheet 23 is coated with adhesive. Any adhesive or glue used in the art for such purposes can be used for the adhesive herein, with pressure-sensitive adhesives being preferred. Suitable adhesives are manufactured by H. B. Fuller Company of St. Paul, Minn., under the designation 2238. Suitable adhesive fasteners are also described in U.S. Pat. No. 4,917,697. Before the sanitary napkin is placed in use, the pressure-sensitive adhesive is typically covered with a removable release liner 37 in order to keep the adhesive from drying out or adhering to a surface other than the crotch portion of the panty prior to use. Suitable release liners are also described in the above-referenced U.S. Pat. No. 4,917,697. Any commercially available release liners commonly used for such purposes can be utilized herein. A non-limiting example of a suitable release liner is BL30MG-A Silox 4P/O, which is manufactured by the Akrosil Corporation of Menasha, Wis. The sanitary napkin 20 of the present invention is used by removing the release liner and thereafter placing the sanitary napkin in a panty so that the adhesive contacts the panty. The adhesive maintains the sanitary napkin in its position within the panty during use.

In a preferred embodiment of the present invention, the sanitary napkin has two flaps 34 each of which are adjacent to and extend laterally from the side edge of the absorbent core. The flaps 34 are configured to drape over the edges of the wearer's panties in the crotch region so that the flaps are disposed between the edges of the wearer's panties and the thighs. The flaps serve at least two purposes. First, the flaps help serve to prevent soiling of the wearer's body and panties by menstrual fluid, preferably by forming a double wall barrier along the edges of the panty. Second, the flaps are preferably provided with attachment means on their garment surface so that the flaps can be folded back under the panty and attached to the garment facing side of the panty. In this way, the flaps serve to keep the sanitary napkin properly positioned in the panty. The flaps can be constructed of various materials including materials similar to the topsheet, backsheet, tissue, or combination of these materials. Further, the flaps may be a separate element attached to the main body of the napkin or can comprise extensions of the topsheet and backsheet (i.e., unitary). A number of sanitary napkins having flaps suitable or adaptable for use with the sanitary napkins of the present invention are disclosed in U.S. Pat. No. 4,687,478 entitled "Shaped Sanitary Napkin With Flaps", which issued to Van Tilburg on Aug. 18, 1987; and U.S. Pat. No. 4,589,876 entitled "Sanitary Napkin", which issued to Van Tilburg on May 20, 1986. The disclosure of each of these patents is hereby incorporated herein by reference.

In a preferred embodiment of the present invention, an acquisition layer(s) 25 may be positioned between the topsheet 22 and the absorbent core 24. The acquisition layer 25 may serve several functions including improving wicking of exudates over and into the absorbent core. There are several reasons why the improved wicking of exudates is important, including providing a more even distribution of the exudates throughout the absorbent core and allowing the sanitary to be made relatively thin. The wicking referred to herein may encompass the transportation of liquids in one, two or all directions (i.e., in the x-y plane and/or in the z-direction). The acquisition layer may be comprised of several different materials including nonwoven or woven webs of synthetic fibers including polyester, polypropylene, or polyethylene; natural fibers including cotton or cellulose; blends of such fibers; or any equivalent materials or combinations of materials. Examples of sanitary napkins having an acquisition layer and a topsheet are more fully described in U.S. Pat. No. 4,950,264 issued to Osborn and U.S. patent application Ser. No. 07/810,774, "Absorbent Article Having Fused Layers", filed Dec. 17, 1991 in the names of Cree, et al. The disclosures of each of these references are hereby incorporated herein by reference.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

Wihat is claimed is:

1. An absorbent structure comprising:
   (a) an apertured polymeric film web comprising a first surface, a second surface generally parallel to and spaced apart from said first surface, and a plurality of fluid passageways, said fluid passageways being formed by a three-dimensional network of interconnecting elements extending between said first surface and said second surface to place said first surface and said second surface in fluid communication with one another, said web being formed of a polymeric film comprising at least one bulk modified layer, wherein said bulk modified layer comprises a substantially homogeneous stabilized two-phase dispersion comprising a low surface energy, hydrophobic additive dispersed in a polymeric material;
   (b) a hydrophilic absorbent core positioned adjacent the second surface of said web; wherein a surface energy gradient is produced between said hydrophobic topsheet and said hydrophilic absorbent core whereby aqueous fluid is effectively transported away from the first surface of the web.

2. The web of claim 1, wherein said hydrophobic additive comprises polydimethylsiloxane.

3. The web of claim 2, wherein said polydimethylsiloxane is dispersed in said bulk modified layer at a level between about 1.5% and about 5.0% by weight.

4. The web of claim 1, wherein said polymeric material comprises polyolefinic material.

5. The web of claim 4, wherein said polyolefinic material is a polyethylene.

6. The web of claim 4, wherein said polyolefinic material is a blend of linear low density polyethylene and low density polyethylene.

7. The web of claim 1, wherein said bulk modified layer exhibits a contact angle with water greater than 90 degrees.

8. An absorbent article comprising:
   (a) a topsheet comprising an apertured polymeric film web having a first surface, a second surface generally parallel to and spaced apart from said first surface, and a plurality of fluid passageways, said fluid passageways being formed by a three dimensional network of interconnecting elements extending between said first surface and said second surface to place said first surface and said second surface in fluid communication with one another, said web being formed of a polymeric film comprising at least one bulk modified layer, wherein said bulk modified layer comprises a substantially homogeneous stabilized two-phase dispersion of a low surface energy, hydrophobic additive in a polymeric material,
   (b) a backsheet peripherally joined with said topsheet; and
   (c) a hydrophilic absorbent core positioned between the second surface of said topsheet and said backsheet;
   wherein a surface energy gradient is produced between said hydrophobic topsheet and said hydrophilic absorbent core whereby fluid is effectively transported away from the first surface of the web.

9. The absorbent article of claim 8, wherein said hydrophobic additive comprises polydimethylsiloxane.

10. The absorbent article of claim 9, wherein said polydimethylsiloxane is dispersed in said bulk modified layer at a level between about 1.5% and about 5.0% by weight.

11. The absorbent article of claim 8, wherein said polymeric material comprises polyolefinic material.

12. The absorbent article of claim 11, wherein said polyolefinic material is a polyethylene.

13. The absorbent article of claim 11, wherein said polyolefinic material is a blend of linear low density polyethylene and low density polyethylene.

14. The absorbent article of claim 8, wherein said bulk modified layer exhibits a contact angle with water greater than 90 degrees.

15. An absorbent article comprising:
   (a) a topsheet comprising an apertured polymeric film web having a first surface, a second surface generally parallel to and spaced apart from said first surface, and a plurality of fluid passageways, said fluid passageways being formed by a three dimensional network of interconnecting elements extending between said first surface and said second surface to place said first surface and said second surface in fluid communication with one another, said web being formed of a polymeric film comprising at least one bulk modified layer, wherein said bulk modified layer comprises a substantially homogeneous stabilized two-phase dispersion of a low surface energy, hydrophobic additive in a polymeric material, said second surface of said topsheet including a hydrophilic adhesive deposited thereon;
   (b) a backsheet peripherally joined with said topsheet; and
   (c) a hydrophilic absorbent core positioned between the second surface of said topsheet and said backsheet, said second surface of said topsheet being joined to said absorbent core by said hydrophilic adhesive;
   wherein a surface energy gradient is produced between the relatively hydrophobic topsheet and said hydrophilic adhesive and said absorbent core whereby fluid is effectively transported away from the first surface of the web.

16. The absorbent article of claim 15, wherein said hydrophilic adhesive is deposited in a discontinuous pattern.

17. The absorbent article of claim 15, wherein said hydrophobic additive comprises polydimethylsiloxane.

18. The absorbent article of claim 15, wherein said polydimethylsiloxane is dispersed in said bulk modified layer at a level between about 1.5% and about 5.0% by weight.

19. The absorbent article of claim 15, wherein said polymeric material comprises polyolefinic material.

20. The absorbent article of claim 19, wherein said polyolefinic material is a polyethylene.

21. The absorbent article of claim 19, wherein said polyolefinic material is a blend of linear low density polyethylene and low density polyethylene.

22. The absorbent article of claim 15, wherein said hydrophilic adhesive comprises a hot melt adhesive with a resin incorporated surfactant.

23. The absorbent article of claim 22, wherein said first surface exhibits a contact angle with water greater than 90 degrees and said hydrophilic adhesive reduces the surface tension of water by at least 20%.

* * * * *

UNITED STATES PATENT AND TRADEMARK OFFICE
CERTIFICATE OF CORRECTION

PATENT NO.   : 6,291,050 B1
DATED        : September 18, 2001
INVENTOR(S)  : Cree et al.

It is certified that error appears in the above-identified patent and that said Letters Patent is hereby corrected as shown below:

Column 3,
Line 24, please delete "U.S. Pat. No.".
Line 25, before "4,324,246" please insert -- U.S. Pat. No. --.

Column 9,
Line 8, please delete "MBO50-002" and insert therefor -- MB050-002 --.

Column 10,
Line 7, please delete "1100°" and insert therefor -- 110° --.
Line 40, please delete "at." and insert therefor -- al. --.

Column 14,
Line 33, after "layer" please insert -- 25 --.
Line 55, please delete "23$a$" and insert therefor -- 24$a$ --.

Column 17,
Line 15, after "sanitary" please insert -- napkin 20 --.
Line 37, please delete "Wihat" and insert therefor -- What --.

Signed and Sealed this

Twenty-eighth Day of January, 2003

JAMES E. ROGAN
*Director of the United States Patent and Trademark Office*